(12) United States Patent
Washburn

(10) Patent No.: US 10,501,891 B1
(45) Date of Patent: Dec. 10, 2019

(54) CROSSLINKING CELLULOSE WITH GLYOXAL TO IMPROVE ABSORPTION PROPERTIES

(71) Applicant: Rayonier Performance Fibers, LLC, Jacksonville, FL (US)

(72) Inventor: Michael Washburn, Brunswick, GA (US)

(73) Assignee: RAYONIER PERFORMANCE FIBERS, L.L.C., Jacksonville, FL (US)

( * ) Notice: Subject to any disclaimer, the term of this patent is extended or adjusted under 35 U.S.C. 154(b) by 0 days.

(21) Appl. No.: 16/257,760

(22) Filed: Jan. 25, 2019

(51) Int. Cl.
| | |
|---|---|
| *D21H 11/00* | (2006.01) |
| *D21C 9/00* | (2006.01) |
| *C08K 5/00* | (2006.01) |
| *C08L 1/00* | (2006.01) |
| *D21H 11/20* | (2006.01) |
| *C08L 1/02* | (2006.01) |
| *C08K 5/07* | (2006.01) |

(52) U.S. Cl.
CPC ............. *D21H 11/20* (2013.01); *C08K 5/07* (2013.01); *C08L 1/02* (2013.01); *C08L 2205/16* (2013.01); *C08L 2312/00* (2013.01); *D21C 9/005* (2013.01)

(58) Field of Classification Search
CPC .......... D21H 11/20; D21C 9/005; C08K 5/07; C08L 1/02; C08L 2205/16
See application file for complete search history.

(56) References Cited

U.S. PATENT DOCUMENTS

| | | |
|---|---|---|
| 3,224,926 A | 12/1965 | Bernardin |
| 3,241,553 A | 3/1966 | Steiger |
| 3,312,521 A | 4/1967 | Stenner et al. |
| 3,700,549 A | 10/1972 | Croon et al. |
| 3,844,880 A | 10/1974 | Meisel, Jr. et al. |
| 4,204,054 A | 5/1980 | Lesas et al. |
| 4,822,453 A | 4/1989 | Dean et al. |
| 4,853,086 A | 8/1989 | Graef |
| 4,888,093 A | 12/1989 | Dean et al. |
| 4,889,595 A | 12/1989 | Herron et al. |
| 4,889,596 A | 12/1989 | Schoggen et al. |
| 4,889,597 A | 12/1989 | Bourbon et al. |
| 5,225,047 A | 7/1993 | Graef et al. |
| 5,366,591 A | 11/1994 | Jewell |
| 5,447,977 A | 9/1995 | Hansen et al. |
| 5,556,976 A | 9/1996 | Jewell |
| 5,562,740 A | 10/1996 | Cook et al. |
| 5,916,418 A | 6/1999 | Frank et al. |
| 5,998,511 A | 12/1999 | Westland et al. |
| 6,207,278 B1 | 3/2001 | Jewell et al. |
| 6,300,259 B1 | 10/2001 | Westland et al. |
| 6,551,706 B1 | 4/2003 | Jewell et al. |
| 7,074,301 B2 | 7/2006 | Hamed et al. |
| 7,288,167 B2 | 10/2007 | Sears et al. |
| 2005/0016698 A1 | 1/2005 | Stoyanov et al. |
| 2005/0016699 A1 | 1/2005 | Stoyanov et al. |
| 2005/0019563 A1 | 1/2005 | Stoyanov et al. |
| 2005/0019569 A1 | 1/2005 | Stoyanov et al. |

FOREIGN PATENT DOCUMENTS

| | | |
|---|---|---|
| EP | 0 427 361 | 11/1990 |
| EP | 1 745 175 | 1/2007 |
| WO | 2005/108669 | 11/2005 |

*Primary Examiner* — Sikarl A Witherspoon

(74) *Attorney, Agent, or Firm* — Wenderoth, Lind & Ponack, L.L.P.

(57) ABSTRACT

The present invention is directed to a novel dialdehyde based reagent that is neutralized, wherein the preparation of the reagent includes the steps of provide a dialdehyde; provide a caustic soda; mix both reagents until pH of the dialdehyde is 5.5 to 7.5; and stir the mixture.

20 Claims, 1 Drawing Sheet

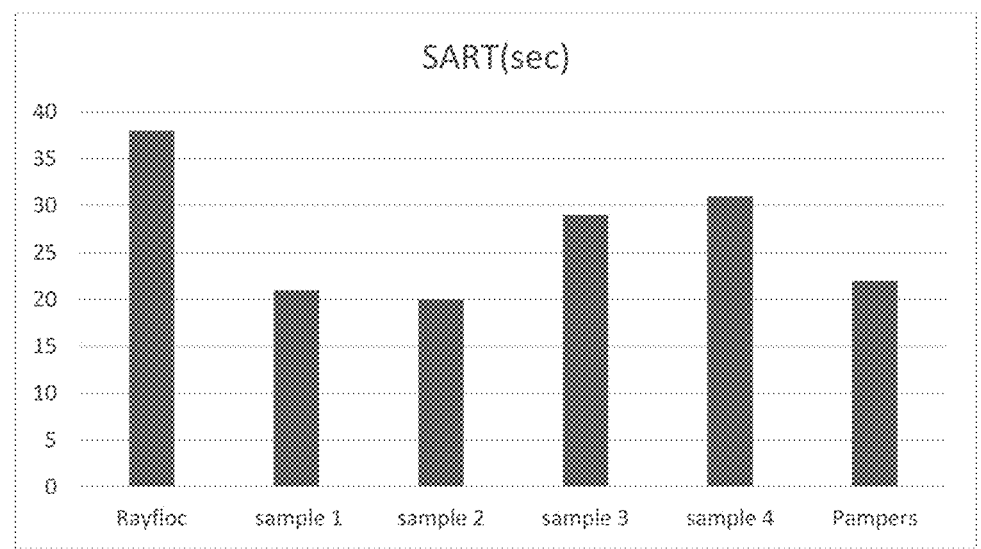

CROSSLINKING CELLULOSE WITH GLYOXAL TO IMPROVE ABSORPTION PROPERTIES

FIELD OF THE INVENTION

The present invention relates to cellulose fibers combined with a Glyoxal (a dialdehyde) based material able to modify the fiber properties by bonding simultaneously to multiple cellulosic chains. Thus, producing wood pulp with modified functionality suitable for use as a surge layer in an absorbent article intended for body waste management. The monomer based material is made from two reagents, a dialdehyde and caustic soda. Embodiments of the present invention relate to a process of neutralizing the glyoxal and using it for making a surge fiber. Another embodiment of the present invention relates to a process of using the surge fibers as a surge layer in an absorbent article.

BACKGROUND OF THE INVENTION

Absorbent articles intended for body fluid management typically are comprised of a top sheet, an ADL (acquisition distribution layer), a back sheet, an absorbent core located between the ADL and back sheet, and an optional surge layer located below the top sheet/ADL and over the absorbent core. The surge layer is mainly comprised of cross-linked cellulosic fibers. A surge layer composed of cross-linked fibers usually provides better transfer and distribution of liquid, increases rate of liquid absorption, reduces gel blocking, and improves surface dryness.

Methods of making cross-linked fiber are described in several patents like U.S. Pat. Nos. 4,204,054; 3,844,880; 3,700,549; 3,241,553; 3,224,926; 7,074,301; and 7,288,167; European Patent No. 0,427,361 B1; and European Patent No. 1,745, 175 A4, the disclosures of which are incorporated by reference herein in their entirety.

Crosslinking is usually carried out at a temperature of over 160° C. Exposing pulp to such high temperature causes yellowing. Another major issue is that the cross-linking is carried at low pH using an acidic crosslinking agent with pH of about 2.5. So, produced fibers have highly acidic properties (very low pH), due to residual unreacted carboxyl groups present on crosslinking agent. Fiber with very low pH may cause skin irritation when used in absorbent article intended for body waste management.

It is therefore, an object of the present invention to provide a crosslinking agent for making fiber with modified functionality and process of making the fiber at milder temperature and near neutral pH. The fiber is suitable for use as a liquid transfer in absorbent articles intended for body waste management.

Another goal of the present invention is to make such transfer pulp free from the before-mentioned disadvantages such as yellowing, low pH and high content of knots and fines.

SUMMARY OF THE INVENTION

There is a need for a simple, relatively inexpensive reagent(s) that reacts with cellulosic chains at a moderate temperature and neutral pH or close to neutral to produce liquid transfer with attractive specifications such as low contents of knots and fines, low discoloration, and can be defiberized without a serious damage to the fibers.

It is therefore a feature of an embodiment of the invention to provide an dialdehyde based crosslinking reagent able to react with cellulose chains and produce pulp with modified properties suitable for use as liquid transfer fiber in an absorbent article intended for body waste management. It also is a feature of an embodiment of the present invention to provide a method of making the cellulosic based transfer fiber in a sheet form using the aldehyde based crosslinking reagent of the present invention. Wherein, defiberization produces fluff with high brightness and reduced contents of knots, nits, and fines. It is yet another feature of an embodiment of the present invention to provide a method of making the cellulosic based surge fibers in the fluff form using the crosslinking reagent of the present invention. It is yet another embodiment of the present invention to make a surge layer from the surge fiber of the present invention that improves centrifuge retention capacity, absorption capacity, absorption rate, absorbency under load of an absorbent article.

In yet another feature of an embodiment of the present invention, the surge fibers may be utilized as a surge layer or in the absorbent core of an absorbent article.

In accordance with these and other features of embodiments of the invention, there is provided a dialdehyde based crosslinking reagent useful for making cellulosic based surge pulp. The reagent is a glyoxal reacted with caustic soda, and the end groups are substituents able to form covalent bonds with the hydroxyl groups of the cellulose chain at relatively low to moderate temperature. The term "glyoxal" as used in this specification has two meanings. The first meaning is in reference to the specific dialdehyde compound. The second meaning is in reference to any dialdehyde suitable to react with caustic soda to form a crosslinking agent for cellulose fibers.

In accordance with an additional feature of an embodiment of the present invention, the method provided of making cellulosic based transfer pulp that includes applying a solution of the polymeric based crosslinking reagent of the present invention to cellulosic fibers in sheet form to impregnate the fibers, then drying the impregnated cellulosic fibers.

These and other objects, features and advantages of the present invention will appear more fully from the following detailed description of the preferred embodiments of the invention.

BRIEF DESCRIPTION OF THE DRAWINGS

FIG. 1 is a bar chart showing the liquid absorption properties of four samples of cellulose based transfer fibers of the invention compared with two commercial brands using the SART test method.

DETAILED DESCRIPTION OF THE INVENTION

The present invention is a glyoxal based crosslinking reagent which is made from reacting a dialdehyde compound with a caustic soda. The glyoxal is especially useful for making a liquid transfer pulp with high brightness and improved absorption under load. The liquid transfer pulp of the present invention is especially useful for use in an absorbent article structure.

Embodiments of the present invention may be used with any classes of absorbent structures, without limitation, whether disposable or otherwise. Without being limited to a specific theory, glyoxal acts as a crosslinker. As such, glyoxal disrupt the hydrogen bonding sites by occupying the space between the cellulosic chains, thereby reducing interfiber bonding, thus enhancing the fluffing properties of the transfer fiber and reducing knots and knits after defiberization. The aldehydes serve to bridge the adjacent cellulosic chains through bonding to their hydroxyl groups, thereby increasing the resiliency and porosity of the fibers.

Another embodiment of the present invention concerns cellulosic based transfer pulp made from reacting the aldehyde based crosslinker with cellulosic fibers. Produced cellulosic based pulp of the present invention is useful in absorbent articles, and especially in forming a surge layer or an absorbent core in an absorbent article. The precise construction of the absorbent article is not critical to the present invention, and any absorbent article can benefit from this invention.

Suitable absorbent garments are described, for example, in U.S. Pat. Nos. 5,281,207, and 6,068,620, the disclosures of each of which are incorporated by reference herein in their entirety including their respective drawings. Those skilled in the art will can utilize the surge fibers of the present invention in an absorbent garment, core, acquisition layer, and the like, using the guidelines provided herein.

Any dialdehyde compound capable of reacting with caustic soda to produce a glycolate compound able to react simultaneously with the hydroxyl groups of the cellulosic chains may be used in the present invention. Examples of suitable dialdehydes are aliphatic and aromatic dialdehydes. Any caustic soda capable of neutralizing glyoxal may be used. Examples of caustic soda are sodium hydroxide and potassium hydroxide. If potassium hydroxide is used with glyoxal, potassium glycolate is produced. If sodium hydroxide is used, sodium glycolate is produced.

Examples of dialdehydes are: glyoxal, glutaraldehyde, 1,4-cyclohexane dicarbaldehyde, 1,3-cyclohexane dicarbaldehyde, and the mixtures and combinations thereof.

Preferred dialdehydes are glyoxal, glutaraldehyde and 1,4-cyclohexane dicarbaldehyde.

The glyoxal reagent may be prepared by any suitable and convenient procedure. The caustic soda is used to raise the pH of Glyoxal from about 2.5 to 5.5 to 7.5.

The reaction may be carried out at room temperature. Preferably, the reaction is carried out at room temperature for about 1 min and up to 60 min. The product of the reaction is water-soluble, and can be diluted with water to any desirable concentration.

Another aspect of the present invention provides a method for making the liquid transfer pulp using the glyoxal based cross-linking agent described above. The process preferably comprises treating cellulose fibers in sheet or roll form with an aqueous solution of glyoxal based cross-linking agent, followed by drying at sufficient temperature and for a sufficient period to remove water and accelerate the covalent bond between hydroxyl groups of cellulose fibers and the reagent. Using the guidelines provided herein, those skilled in the art can determine suitable drying and curing temperatures and times.

Cellulosic fibers suitable for use in the present invention include those primarily derived from wood pulp. Suitable wood pulp can be obtained from any of the conventional chemical processes, such as the kraft and sulfite processes. Preferred fibers are those obtained from various softwood pulps such as southern pine, white pine, Caribbean pine, western hemlock, various spruces, (e.g. sitka spruce), Douglas fir or mixtures and combinations thereof. Fibers obtained from hardwood pulp sources, such as gum, maple, oak, eucalyptus, poplar, beech, and aspen, or mixtures and combinations thereof also can be used in the present invention. Other cellulosic fibers derived from cotton linters, bagasse, kemp, flax, and grass also may be used in the present invention. The fibers can be comprised of a mixture of two or more of the foregoing cellulose pulp products. Particularly preferred fibers for use in the making transfer layer of the present invention are those derived from wood pulp prepared by the kraft and sulfite pulping processes.

The cellulosic fibers can be produced in a variety of forms. For example, one aspect of the present invention contemplates using cellulosic fibers in sheet or roll form.

Preferably the glyoxal based cross-linking reagent, after being prepared is diluted with water to a concentration sufficient to provide from about 0.5 to 3.0 wt. % of reagent on pulp. For example, 3 wt. % of glyoxal based cross-linking reagent means 3.0 g of the glyoxal based cross-linking reagent per 100 g oven dried pulp.

Any method of applying a solution of glyoxal based cross-linking agent to the pulp may be used. The method preferably leads to an impregnation of the cellulose fiber with the solution of the glyoxal based cross-linking reagent, whereby the glyoxal based cross-linking reagent may be adhered to the fibers, adsorbed on the surface of the fibers, or linked via chemical, hydrogen or other bonding (e.g., Van der Waals forces) to the fibers. Acceptable methods include, for example, spraying, dipping, and rolling.

Preferably, fiber in sheet form is preferably impregnated with a solution of the glyoxal based cross-linking reagent and pressed for uniform distribution of the reagent. Fibers in the roll form are conveyed through a treatment zone where the crosslinking agent solution is applied on both surfaces by conventional methods such as spraying, rolling, dipping, knife-coating or any other manner of impregnation. A preferred method is adding an aqueous solution containing the glyoxal based cross-linking reagent to a fully bleached dried pulp in sheet form then pressing to a desired solution pick-up.

Fibers in a roll or sheet form after treatment with the glyoxal based cross-linking reagent are preferably dried in a one step process. Such drying removes water from the fibers, thereupon inducing the formation of acetal σ-bonds between hydroxyl groups of the cellulosic chains and the glyoxal based cross-linking agent.

Drying typically is carried out in a dryer having a temperature from about 130° C. to about 160° C. Cure temperature must be between 110 and 130° C. If sheet temperature exceeds 135° C., yellowing and low brightness occurs. Drying is preferably carried out for a sufficient period to permit complete fiber drying and efficient bonding between cellulosic fibers and the glyoxal based cross-linking reagent. Preferably, the fibers are dried from seconds to minutes.

To obtain a short drying time, it is necessary that, the water in the wet pulp is removed substantially. Water removal is conventionally achieved by mechanical means such pressing.

The cellulosic based surge fiber made in accordance with embodiments of the present invention preferably possess characteristics that are desirable as a surge layer in absorbent articles.

The surge fibers also preferably possess characteristics making it suitable for use as a surge layer in absorbent articles, like having a liquid centrifuge retention capacity (CRC) not higher than 0.65 grams of synthetic urine per gram of fiber at a centrifuge speed of 1300 rpm (hereinafter "g/g"). The centrifuge retention capacity measures the ability of the fibers to retain fluid against a centrifugal force.

The surge fibers preferably have a free swell (FS) greater than about 9.0 g/g, and absorbency under load of 0.3 psi of greater than about 8.0 g/g.

The free swell measures the ability of the fibers to absorb fluid without being subjected to a confining or restraining pressure. The absorbency under load measures the ability of the fibers to absorb fluid against a restraining or confining force of 0.3 psi. The liquid retention under centrifuge, free swell, and absorbency under load preferably are determined by the hanging cell test method described in the example section.

There are other advantages for the surge fibers of the present invention. Preferably surge fibers made in accordance with the present invention contains less than 30.0% knots and fines and have ISO brightness of over 80%.

The properties of the surge fibers prepared in accordance with the present invention make the fibers suitable for use, for example, as a bulking material, in the manufacturing of high bulk specialty fibers that require good absorbency and porosity. The surge fibers can be used, for example, in absorbent products. The fibers may also be used alone, or preferably incorporated into other cellulosic fibers to form blends using conventional techniques, such as air laying techniques. In an airlaid process, the transfer fibers of the present invention alone or in combination with other fibers are blown onto a forming screen or drawn onto the screen via a vacuum. Wet laid processes may also be used, combining the cellulosic based transfer fibers of the invention with other cellulosic fibers to form sheets or webs of blends.

The cellulosic based surge fibers of the present invention may be incorporated into various absorbent articles, preferably intended for body waste management such as adult incontinent pads, feminine care products, and infant diapers. The cellulosic based surge fibers can be used as a transfer layer in the absorbent articles, wherein it placed as a separate layer on top of the absorbent core, and it can be utilized in the absorbent core of the absorbent articles in a blend with SAP or without. Towels and wipes also may be made with the cellulosic fibers of the present invention, and other absorbent products such as filters.

The surge fibers of the present invention were incorporated into an absorbent article as a surge layer, and evaluated by the several tests shown in the examples section such as a Specific Absorption Rate Test (SART). The tests results show that the absorbent article that contained the surge fibers of the present invention provided results comparable to those obtained by using commercial cross-linked fibers, especially those like curly fibers.

In order that various embodiments of the present invention may be more fully understood, the invention will be illustrated, but not limited, by the following examples. No specific details contained therein should be understood as a limitation to the present invention except insofar as may appear in the appended claims.

EXAMPLES

The following test methods were used to measure and determine various physical characteristics of the inventive cellulosic based transfer fibers.

Hanging Cell Test Method

The absorbency test method was used to determine the absorbency under load, free swell, and centrifuge retention capacity. The test was carried out in a one inch inside diameter plastic cylinder having a 100-mesh metal screen adhering to the cylinder bottom "cell," containing a plastic spacer disk having a 0.995-inch diameter and a weight of about 4.4 g. In this test, the weight of the cell containing the spacer disk was determined to the nearest 0.001 g, and then the spacer was removed from the cylinder and about 0.35 g (dry weight basis) of cellulosic based transfer fibers were air-laid into the cylinder. The spacer disk then was inserted back into the cylinder on the fibers, and the cylinder group was weighed to the nearest 0.001 g. The fibers in the cell were compressed with a load of 4.0 psi for 60 seconds, the load then was removed and fiber pad was allowed to equilibrate for 60 seconds. The pad thickness was measured, and the result was used to calculate the dry bulk of cellulosic based transfer fibers.

A load of 0.3 psi was then applied to the fiber pad by placing a 100 g weight on the top of the spacer disk, and the pad was allowed to equilibrate for 60 seconds, after which the pad thickness was measured, and the result was used to calculate the dry bulk under load of the cellulosic based transfer fibers. The cell and its contents then were hanged in a Petri dish containing a sufficient amount of saline solution (0.9% by weight saline) to touch the bottom of the cell. The cell was allowed to stand in the Petri dish for 10 minutes, and then it was removed and hanged in another empty Petri dish and allowed to drip for about 30 seconds. The 100 g weight then was removed and the weight of the cell and contents was determined. The weight of the saline solution absorbed per gram fibers then was determined and expressed as the absorbency under load (g/g). The free swell of the cellulosic based transfer fibers was determined in the same manner as the test used to determine absorbency under load above, except that this experiment was carried using a load of 0.01 psi. The results are used to determine the weight of the saline solution absorbed per gram fiber and expressed as the absorbent capacity (g/g).

The cell then was centrifuged for 3 min at 1400 rpm (Centrifuge Model HN, International Equipment Co., Needham HTS, USA), and weighed. The results obtained were used to calculate the weight of saline solution retained per gram fiber, and expressed as the retention after centrifuge (g/g).

Fiber Quality

Fluff Fiberization Measuring Instrument is used to measure knots and fines content of fibers. In this instrument, a sample of transfer fibers in defiberized form was continuously dispersed in an air stream. During dispersion, loose fibers passed through a 16 mesh screen (1.18 mm) and then through a 42 mesh (0.36 mm) screen. Pulp bundles (knots) which remained in the dispersion chamber and those that were trapped on the 42-mesh screen were removed and weighed. The formers are called "knots" and the latter "accepts." The combined weight of these two was subtracted from the original weight to determine the weight of fibers that passed through the 0.36 mm screen. These fibers were referred to as "fines."

Examples 1 illustrates a representative method for making a solution of glyoxal based crosslinking reagent of an embodiment of the present invention and use it in making surge fibers in sheet and fluff form using the impregnation technique.

Example 1

To a solution of glyoxal in water (20.0 g of 400, solution) was added sodium hydroxide 50% (2 drops) to bring the pH from 2.3 to 7.2. The produced solution was stirred at room temperature for 5 min. Water was then added to adjust the total weight of the solution to 400 g (final concentration of glyoxal reagent is 2.0% by weight).

The produced solution was added to a plastic tray, a sheet of Rayfloc-J-LDE (12×12 inch$^2$, basis weight 720 gsm) was dipped into the solution then pressed to achieve the desired level of glyoxal reagent on pulp (about 2.0 wt %). Several sheets were prepared in the same manner and dried in an oven as shown in Table I. Prepared sheets of transfer fibers were defiberized by feeding them through a hammermill and produced fluff was evaluated by hanging cell test and fiber quality test. Test results are summarized in Tables I and II.

TABLE I

| | | | | Hanging cell test results (g/g) | | |
|---|---|---|---|---|---|---|
| Sample | Drying Temp (deg C.) | Sheet Temp (deg C.) | Brightness | Absorbancy Under Load | Free Swell | Centrifuge Retention Capacity |
| 1 | 120 | 110 | 84.6 | 8.07 | 9.09 | 0.54 |
| 2 | 130 | 120 | 81.8 | 8.37 | 9.36 | 0.55 |
| 3 | 140 | 130 | 81 | 8.4 | 9.65 | 0.55 |
| 4 | 145 | 135 | 85.4 | 8.04 | 9.11 | 0.54 |
| Rayfloc-JLDE | | | 85 | 7.87 | 8.8 | 0.77 |

TABLE II

| Sample | Kamas Energy (Watts/kg) | Johnson Classification (%) | | |
|---|---|---|---|---|
| | | Accepts | Knots | Fines |
| 1 | 45.3 | 71.6 | 19.5 | 8.9 |
| 2 | 49 | 69.6 | 20.8 | 9.6 |
| 3 | 45.2 | 76.7 | 14.8 | 8.5 |
| 4 | 42.7 | 64.8 | 27.4 | 7.9 |
| Rayfloc-JLDE | 55.1 | 77.8 | 19.2 | 3 |

Absorption Rate Test (SART)

The cellulosic based transfer fibers made in accordance with an embodiment of the present invention was tested for liquid absorption properties. To evaluate the absorption properties, the absorption time, the time required for a dose of saline to be absorbed completely into the absorbent article was determined.

The Absorption Time was determined by the SART test method. The test was conducted on an absorbent core obtained from a commercially available diaper stage 4 Pampers®. A sample core was cut from the center of the diaper, had a circular shape with a diameter of about 60.0 mm, and an average weight of about 3.0 g (±0.2 g).

In this test, the curly fibers layer of the sample core was replaced with an air-laid pad made from the cellulosic based transfer fibers of an embodiment of the present invention. The fiber pad weighed about 0.7 g and was compacted to a thickness of about 3.0 mm before it was used.

The core sample including the surge layer was placed into the testing apparatus. The apparatus with a load of 0.7 psi and its contents were placed on a leveled surface and dosed with three successive insults, each being 9.0 ml of saline solution, (0.9% by weight), the time interval between doses being 10 min. The time in seconds required for the saline solution of each dose to disappear from the funnel cup was recorded and expressed as an absorption time or strikethrough. The third insult strikethrough time is provided in FIG. 1. The data in FIG. 1 includes the results obtained from testing surge layers of commercial cross-linked fibers and conventional uncross-linked fibers. It can be seen from FIG. 1 that, the absorption times of the modified fibers of embodiments of the present invention are as good as or better than the acquisition time for the commercial cross-linked fibers such as curly fibers.

The invention claimed is:

1. A dialdehyde based reagent, which consists of:
a solution of dialdehyde and a caustic soda in water, wherein the solution has a pH of about 5.5 to 7.5, and wherein the dialdehyde is 2.0% by weight in the solution.

2. The dialdehyde based reagent of claim 1, wherein the reagent is suitable for making liquid surge fiber.

3. The dialdehyde based reagent of claim 2, wherein the surge fiber is useful as a surge layer in an absorbent article.

4. The dialdehyde based reagent of claim 1, wherein the dialdehyde is selected from glyoxal, glutaraldehyde, 1,4-cyclohexane dicarbaldehyde, and 1,3-cyclohexane dicarbaldehyde, and mixtures thereof.

5. The dialdehyde based reagent of claim 1, wherein the caustic soda is sodium hydroxide or potassium hydroxide.

6. A method of making liquid surge fiber, comprising: providing a solution of the dialdehyde based reagent of claim 1; providing cellulosic fiber derived from wood pulp; applying the solution of the dialdehyde based reagent to the cellulosic fibers to impregnate the cellulosic fibers; and drying the treated cellulosic fibers.

7. The method of claim 6, wherein the solution of the dialdehyde based reagent is applied to the cellulosic fiber by spraying, dipping or applying with a puddle press, size press or a blade-coater.

8. The method of claim 6, wherein the cellulosic fiber is provided in sheet or roll form.

9. The method of claim 6, wherein the solution of the reagent is applied to the cellulosic fibers to provide 1 wt % to about 3 wt % of dialdehyde based reagent on the fiber.

10. The method of claim 6, wherein the cellulosic fiber is a cellulose fiber selected from the group consisting of: hardwood cellulose pulp, softwood cellulose pulp obtained from a kraft or sulfite chemical process, caustic-treated pulp and combinations and mixtures thereof.

11. The method of claim 6, wherein the drying is conducted at a temperature within the range of about 120° C. to about 160° C.

12. The method of claim 6, wherein the treated cellulosic fibers are dried for a period that affords the fibers with a moisture content of less than 7%.

13. A cellulose fiber which is crosslinked by the dialdehyde based reagent of claim 1.

14. An article of manufacture comprising the cellulose fiber of claim 13.

15. A composition consisting of the dialdehyde based reagent according to claim 1 and cellulose fibers derived from wood pulp.

16. A composition according to claim 15, wherein the concentration of the dialdehyde based reagent to cellulose fibers is 0.5 to 3.0 wt % of reagent to fibers.

17. A composition consisting of cellulose fibers derived from wood pulp, which are crosslinked with the dialdehyde based reagent according to claim 1.

18. The composition according to claim 17, wherein the fibers have a free swell (FS) greater than about 9.0 g/g, and an absorbency under load of 0.3 psi of greater than about 8.0 g/g.

19. A method of making a liquid surge fiber, comprising:
providing a solution of the dialdehyde based reagent of claim 1,
applying the solution of the dialdehyde based reagent to cellulosic fibers derived from wood pulp in sheet form to impregnate the cellulosic fibers, removing excess solution from the cellulosic fibers by pressing to a desired pickup, and drying and curing the cellulosic fibers at a temperature not higher than 135° C. for a period sufficient to afford completely dry cellulosic fibers.

20. The method of claim 19, wherein the completely dry cellulosic fibers contain less than 30.0% knots and fines and has and ISO brightness of over 80%.

* * * * *